All the above azo dyes are shown in "Colour Index", 3rd Edition, Vol. 2 (1971) as azo dyes used for dyeing nickel modified polypropylene fiber.

Following conventional methods the printing paste containing a suitable dye may be applied to a polyolefin fabric by a printing block, stencil, roller, or spraying device, after which the printed fabric is dried and optionally steamed if desired, at atmospheric or superatmospheric pressures.

Following the dyeing or printing of the polyolefin composition the colored material may be contacted with a hot aqueous soap solution or a solution of a suitable detergent, rinsed with water, and dried.

The following examples illustrate the invention:

EXAMPLE 1

Preparation of Nickel 3,5-Di-t-Butyl-4-Hydroxybenzoate (NBH)

A slurry of 3,5-di-t-butyl-4-hydroxybenzoic acid (60.0 grams; 0.24 mole) in 600 mls of water is agitated while a solution of sodium hydroxide (19.2 grams of 50% real; 0.24 mole) in 100 mls of water is added thereto at about 40° C. After addition of the sodium hydroxide is completed, the yellowish-colored solution is stirred at about 40°–50° C. for about 0.5 hour and an additional 1.0 gram of 3,5-di-t-butyl-4-hydroxybenzoic acid is added thereto to insure that all of the sodium hydroxide is reacted. The solution, still containing some unreacted acid, is stirred for about 15 hours at room temperature, and filtered through a diatomaceous earth to obtain a clear, pale, lemon-yellow solution. The solution is then diluted with water to a final volume of 1600 mls.

The diluted solution is stirred rapidly at about 40° C. while a solution of nickel chloride hexahydrate (28.6 grams; 0.12 mole) in 300 mls of water is added thereto to form a precipitate of the desired product. After the addition is completed, the slurry is stirred at 35° C. for 2 hours and filtered. The filter cake is then washed with water and dried in a vacuum oven to obtain 63 grams (94% of theoretical) of the desired product.

The nickel salts of 3-methyl-5-t-butyl-4-hydroxybenzoic acid; 3,5-di-t-octyl-4-hydroxybenzoic acid; and 2,6-di-methyl-3,5-di-t-butyl-4-hydroxybenzoic acid are prepared in a similar manner by substituting 0.24 mole of the corresponding acid for the 3,5-di-t-butyl-4-hydroxybenzoic acid.

EXAMPLE 2

Product of the Reaction of Nickel 3,5-Di-t-Butyl-4-Hydroxybenzoate and Diisodecyl Pentaerythrityl Diphosphite A green-colored solution is prepared by dissolving 70 parts by weight of the product of Example 1 and 30 parts by weight of diisodecyl pentaerythrityl diphosphite in 600 parts by weight of toluene at room temperature. The solution is then concentrated under vacuum to remove the toluene and obtain a green-colored solid which is subsequently dried in a vacuum oven at 50° C.

Green-colored solids are obtained in a similar manner by substituting 30 parts by weight of triisodecyl phosphite, distearyl phosphite, tris(nonylphenyl)phosphite, trimethyl phosphite, or trioctadecyl phosphite for the diisodecyl pentaerythrityl disphosphite.

Green-colored solids are obtained in a similar manner by substituting 70 parts of the nickel salt of 3-methyl-5-t-butyl-4-hydroxybenzoic acid, 3,5-di-t-octyl-4-hydroxybenzoic acid, or 2,6-dimethyl-3,5-di-t-butyl-4-hydroxybenzoic acid for the product of Example 1.

EXAMPLE 3

Unstabilized polypropylene (100 parts) is dry blended with 0.2 part of a primary-type phenolic-phosphite antioxidant composition (Cyanox® 1735 Antioxidant; American Cyanamid Company), 0.1 part of calcium stearate and 1 part of the nickel stabilizer compositions described below. The blended mixture is milled on a standard two-roll mill at about 190° C., cut into strips and inserted into a Melt Index Apparatus at 290° C. and an extrudate is removed after 5 to 10 minutes to inspect the composition for thermal discoloration and gassing, as evidenced by bubbles. Each extrudate is assigned a color rating as described previously. The results obtained are listed in Table I.

TABLE I

| Stabilizer Composition* | Discoloration After | | Gassing After | |
|---|---|---|---|---|
| | 5 Min. | 10 Min. | 5 Min. | 10 Min. |
| 100% NBH | 0 | 7 | Bubbling | Bubbling |
| A | 0 | 0 | None | None |
| B | 0 | 0 | " | " |
| C | 0 | 0 | " | " |
| D | 0 | 2 | " | " |

*The stabilizer compositions are the products obtained by reacting 70 parts by weight of NBH with 30 parts by weight of the indicated phosphite, as in Example 2.
A is the diisodecyl pentaerythrityl diphosphite reaction product.
B is the triisodecyl phosphite reaction product.
C is the distearyl phosphite reaction product.
D is the tris(nonylphenyl) phosphite reaction product.

EXAMPLE 4

The dyeability of the polyolefin composition is determined by compression molding the extrudate into thin films (4–5 mils) after blending, milling and aging 10 minutes at 290° C. as described in Example 3. The films are then cleaned by immersion in an aqueous solution (60° C.) containing 0.5% by weight of isooctyl phenoxy polyethoxy ethanol and rinsed with water. The cleansed films are then immersed for 10 minutes in separate aqueous dye baths (95°–100° C.) containing 0.13% by weight of Polypropylene Green BM or Polypropylene Scarlet RBM; each dye bath also contains 2% by weight of citric acid and 0.01% by weight of a nonylphenol ethylene oxide polymer (Deceresol® Surfactant NI; American Cyanamid Company). The dyeability is then qualitatively assessed by visual inspection of the dyed films relative to films containing [2,2'-thiobis(4-t-octylphenolato)]-nbutylamine nickel II (Cyasorb® UV1084 Light Absorber; American Cyanamid Company), a known chelatable dyesite.

The results obtained with 100% NBH and compositions A–D are reported in Table II.

TABLE II

| Stabilizer Composition | Dyeability With | |
|---|---|---|
| | Green BM | Scarlet RBM |
| 100% NBH | Very Good | Very Good |
| A | Excellent | Very Good |
| B | Very Good | Very Good |
| C | Excellent | Very Good |
| D | Good | Very Good |
| UV-1084 | Good | Good |

EXAMPLE 5

The procedures of Examples 3 and 4 are followed utilizing 1 part of nickel stabilizer compositions described below having varying amounts of NBH and

METHOD FOR IMPROVING THE RATE AND MEASUREMENT ACCURACY OF CHEMICAL ANALYSIS

BACKGROUND OF THE INVENTION

In laboratories, absorptiometer, spectrophotometer, nefelometer and fluorometer are generally used as methods to make this measurement. These measurement methods include various difficiencies which have been described in reports in the literature (for example, Clin. Chem. 19, 832, 1973, 20, 1028, 1974, and 21, 249, 1975).

These methods have been improved by the present invention so that the actual measurement can be accurately done. Likewise, the devices have been improved to be more and more automatic and the handling of the measurement results has been automatized (Anal. Chem. 48, 661, 1976).

Furthermore, the transportation and measurement of the reagents before the actual analysis is a great problem. The evaporation of liquid from the reagents and the samples before and during the measurement causes problems to which only little notice has been paid.

Today, both the samples and the reagents are pipetted either manually or automatically. The pipetting is based on volume measurement. The accuracy of the pipetting is usually of the order of $\pm 1$ $\mu l$ and often even poorer (Clin. Chem. 20, 320, 1974). Checking the pipetting result (getting feedback information) is naturally not possible. One must rely on the fact that the pipetting equipment has functioned properly each time and that the pipetter has been very careful each time.

In the literature, a device is described in which the liquid measurement is regulated by a computer. In this system, the weighing scale registers the weight for the liquids to be measured and the weighing scale is connected through the computer to a liquid measuring device in which the liquids to be measured can be regulated to a desired size with 1.0 mg. accuracy (Anal. Chem. 48, 661, 1976). In this system, the liquid evaporation problem has not been solved.

In the measurements described in the beginning, the samples, reagents and reaction mixture (sample and reagents) are usually water solutions or suspensions having characteristics (such as temperature, surface tension, diffusion standards and substance contents) which effect the water evaporation of these solutions. Circumstances of the environment (room temperature, relative humidity and ventilation) and the characteristic of the reagent or sample vessel (diameter, highness, tightness and material) which effect the shape of the liquid surface and so the surface area also effect how fast the liquid evaporates. Furthermore, the evaporation of the samples, reagents and reaction solutions effect the type and construction of the analyzer device in use greatly. Another factor is how much and how carefully trained the user of the device and samples, reagents and reaction solutions, is. The liquid (usually water) evaporation makes the content of other substances in suspension higher by percentage which is greater as the amount of water in the vessel at the beginning is decreased.

The evaporation in various stages cannot be ignored by assuming that it is always standard and that its effect is always the same. In the literature, it has recently been described that the evaporation of water from sample liquids in open vessels causes mistakes in the analysis. Examination of how much of the evaporation of samples and reagents occurs during the stages of the analysis which cause mistakes has not yet been made in total detail. Preliminary experiments show that the evaporation from the generally used cuvettes is about 1 mg./min. (the cuvette opening area is 1 cm$^2$). In other words, if 1000 $\mu l$ reaction solution is preincubated 30 minutes, the evaporation during this period is 30 mg (about 3% of the reaction solution). This would cause a 3% error in the analysis result when measuring in a general photometer.

DETAILED DESCRIPTION OF THE INVENTION

Figure 1:
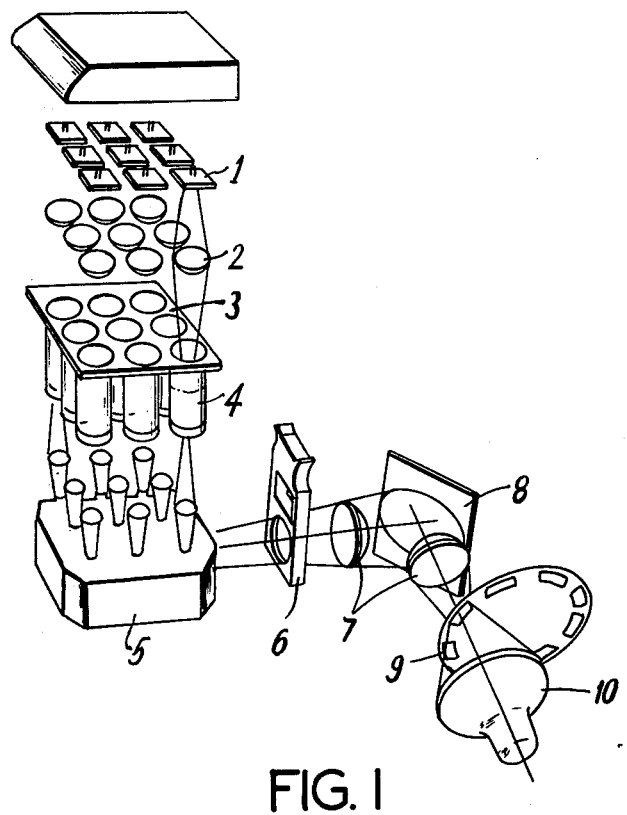
Figure 2:
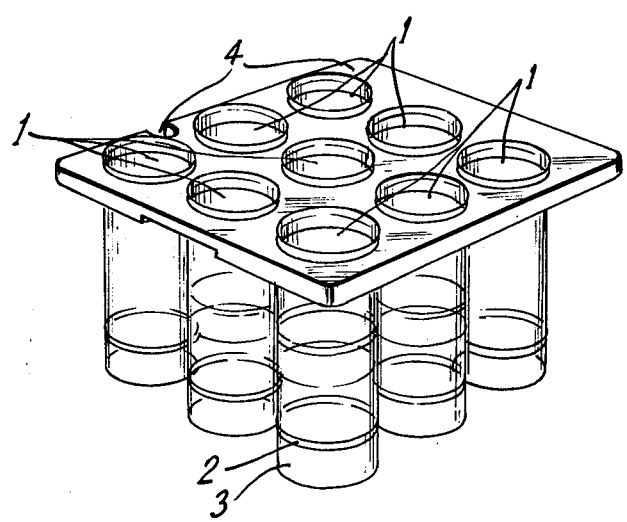

FIGS. 1 and 2 are simplified views in perspective of one embodiment of the apparatus which may be employed for carrying out the invention, reference being made to a more detailed description in my copending U.S. application Ser. No. 672,018, filed Mar. 30, 1976 which is a continuation of my U.S. application Ser. No. 521,453, filed Nov. 6, 1974, now abandoned, the disclosure of said application being incorporated herein by reference.

In the invention described below, the problems caused by inaccurate pipetting of the samples and reagents, lack of the feedback information, the determinate rate, and the sample and reagents evaporation either before or during the analysis are solved. Application example of the method according to the invention:

1. The samples and reagents are stored in a test tube-element equipped with a lid plate. The test tube-element contains an array of nine various tubes which are firmly or loosely mounted a fixed distance apart on a supporting plate. Each tube can be separately closed with a plug on the lid plate. Before analysis, the samples or reagents cannot evaporate from any of the nine tubes in the test tube-element because they are covered.

2. The samples are pipetted one after another from one test tube-element to the tubes of another test tube-element, cuvette or to separate tubes. After each pipetting, the pipetted amount is weighed and the result is transformed to the calculator memory. As was described above, the pipetting accuracy is presently about $\pm 1$ $\mu l$ when the weight can be determined with present devices to 0.1 mg accuracy (with special scales, you can reach even an accuracy of 0.1 $\mu g$). 0.1 mg weight accuracy is about ten times better than 1 $\mu l$ pipette accuracy. Furthermore, when the accurate weight is determined after a "roughly" done sample pipetting, the weight is determined with better accuracy as well as obtaining feedback information about the pipetting. Samples with high viscosity or samples otherwise hard to pipette can be accurately weighed even after an inaccurate pipetting and when calculating the analysis result the weight result is also observed. Solid samples cannot be pipetted; these must be weighed.

3. Both samples and reagents pipetting errors and the evaporation of these substances from the reaction mixture causes errors in the analysis results. If samples and reagents are measured photometrically in a cuvette in which the measuring beam passes through one side of the cuvette, through the measured liquid and then through the other side of the cuvette to the detector (horizontal measure principle), the absorbance can be calculated from the Beer's law:

$A = \epsilon \cdot l \cdot c$

A = absorbance (log Io/I)

$\epsilon$ = molar absorptivity l = the length of the light path (the distance of the one cuvette side to the other)

c = concentration of the absorbing material

It is observed from the above equation that, if the reaction mixture evaporates, the concentration (c) of the absorbing material is growing and causes errors in the absorbance (A). Likewise, the sample and reagent pipetting errors also cause errors in the results.

In the present invention, the measurement is made by the vertical measurement principle where the measurement is made along the vertical longitudinal axis of a cylindrical cuvette, the light beam passing first through the cuvette bottom (optic window), then through the liquid in the cuvette and through the liquid surface to the detector. The opposite direction of the measuring beam is also possible; first through the free liquid surface and liquid and then through the optic window of the cuvette to the detector. FIG. 1 shows an absorption photometer utilizing the vertical measurement principle. The device comprises detectors 1, lenses 2, cuvette block 3, sample 4 in the cuvette, fibre optics member 5, interference filter 6, a lens system 7, semitransparent mirror 8, chopper 9, and lamp 10. FIG. 2 shows a cuvette assembly used with the analyzer of FIG. 1 where on the supporting plate is an array of apertures to hold the nine cuvettes at fixed distances from each other. The cuvette assembly comprises nine cuvettes 1, flat optical window 2, protective rim 3, and orientation-reference notch 4. In the fluorometric can, the primary ray that came through the filter and the monochromator (exitation) moves in a vertical direction and the secondary (emission) from the liquid through the vertical side of the cuvette horizontally through the filter or monochromator to the detector or in the opposite direction.

Beer's law can be transformed into the following form (the FP-9 Analyzer's equation):

Beer's law $A = \epsilon \cdot l \cdot c$ can be transformed by observing that $c = m/v$ and $l = V/a$ in which m = the mass of the absorbing material ($\mu$mol) which is the mass of the material to be analyzed in the cuvette v = the volume of the reaction mixture in the cuvette, ml a = the bottom area of the cuvette ($=0.760 \pm 0.002$ cm$^2$ according to the cuvette in FIG. 2)

to the form $$A = (\epsilon/a) \cdot m \qquad (2)$$

In analysis where the molar absorptivity of the measured material is not used ($\epsilon$) the measured values are compared to the values given by the standard curves which may be described in the form:

$$A = f(m) \qquad (3)$$

Usually the measurements are done in a region of the standard curve that is linear. In this case, the equation may be written in terms of a constant coefficient k in the following form:

$$A = k \cdot m \qquad (4)$$

The coefficient k can be separately determined for each analyzing method and, in practice, should be determined for each device.

It is observed that the absorbance depends only on the mass of the measured material in the cuvette (m). When measuring according to the vertical measurement principle, the concentration of the measured material in the cuvette (c) does not effect the absorbance and, through this, the result. When the water evaporates in the cuvette, the concentration (c) of the measured material grows but the mass (m) remains unchanged.

The evaporation of water from the reaction mixture during the analysis does not cause errors when measuring according to the vertical measurement principle in the direction of the measuring beam in an equal thick cuvette, where the water evaporation shortens the light path in the reaction mixture and this shortening of the light path adds in the same respect as the concentration of the measured material (compare equation $A = \epsilon \cdot l c$, where $\epsilon$ = standard, l = length of the lightpath and c = the content of the measured material.

During the preparation of reaction mixture, errors made in pipetting reagents will cause errors in the concentration of the material to be measured in the reaction mixture; whereas, the mass (m) of the measured material remains unchanged in the cuvette. When measuring according to the vertical measurement principle, the pipetting errors of the reagents are compensated so that they do not cause errors in the result.

During various stages of the analysis, water evaporates, for example, during centrifugation, preincubating waiting and measuring, and the concentration (c) of the measured material in the reaction mixture may grow, but its mass (m) remains unchanged. In the vertically measuring absorption photometer (as in other previously mentioned instruments equipped with the vertical measurement principle), the error is compensated for because the mass (m) of the material in the liquid is measured. For the same reason, when measuring according to the vertical measuring principle, the changes of the contents of the reagents caused by the evaporation are compensated for.

The following improvements are described in a summary.

1. Water is unable to evaporate from the samples when they are enclosed in a test tube element equipped with a lid plate; therefore, a 25 to 50% error margin is avoided in the analysis results. Likewise, water evaporation from the reagents is avoided.

2. The samples can be measured by weighing with ten times more accuracy than by pipetting and, at the same time, feedback information about the pipetting is given.

Particularly small samples (for instance, under 20 $\mu$l, about 20 mg) can be measured with 0.1 mg accuracy. In fluorometric measurements where the sensitivity can be $10^3 - 10^4$ times greater than in photometric measurements, the sample can be, for instance, 1 $\mu$l. Then weighing of the sample is necessary to avoid gross mistakes in the results (when pipetting a sample of 1 $\mu$l size, the error can be over 50%).

3. If the sample is solid or hard to pipette, the weighing of the sample is the only way to measure the sample accurately. The measured result given by the analytic device as well as the weight of the sample are used by the calculator to derive the final result. It is possible to use this procedure, for instance, in the determination of grain protein with the DBC method. (J. Biol. Chem., 154, 239, 1944, Cereal Chem., 33, 190, 1956, J. Sci. Food Agric., 10, 425, 1959, Brit. J. Nutr., 18, 537, 1964, Curr. Sci., 38, 330, 1969 and IAEA-PL-570/17, 145, 1975).

4. At the measurement wavelength, the pipetting errors of non-absorbing reagents (often 1 to 5%) do not cause errors in the results when measurement is performed according to the vertical measurement principles. The effect of light-absorbing reagents on the result can, if necessary, be eliminated by weighing after they are pipetted.

5. The evaporation of the liquid from the reaction mixture during the various stages of the analysis does not cause errors in the results thanks to the vertical measurement. In the above-described devices operating according to the horizontal measurement principle, the evaporation of, for instance, 0.1 - 0.3 ml from the reaction mixture causes an error of about 3 - 10% if the analysis takes 30 minutes' time and the cuvette opening is 1 cm$^2$.

Characteristics for the before-described invention are:

1. The sample is pipetted and weighed and the weight result is transferred to the calculator memory. Solid samples are only weighed. Samples are stored in a closed test tube element.

2. The reagents are pipetted and, if necessary, weighed and the results transferred to the calculator memory.

3. Measurement of the reaction mixture (sample and reagents) is performed photometrically according to the vertical measurement principle, where Absorbance = standard × the mass of the measured material. The same is also valid even if measurement is performed according to the longitudinal measurement principle as, for instance, emission (fluorometric) or turbidity (nefelometric).

4. In the method according to the invention, the weighing device as well as the analysis device are connected to a programmed calculator or microprocessor. In the calculation phase, the automatic calculator program observes the measurement result, as well as the weight of the sample and, when necessary, also the weights of the reagents calculating the final analysis and displaying them in desired units. It is natural that the above-described invention can be applied in manual and semi or fully automatic devices which, furthermore, can be one or several channel procedures.

What I claim:

1. A method of improving the measuring accuracy in the chemical analyses of solutions containing substances to be measured using a single or a multi-channel optical measuring device together with gravimetric measurements of said solutions which comprises:

providing at least one of said solutions to be measured confined in a closed space to minimize evaporation thereof, removing a volumetric portion of said solution to be analyzed from said confined space and inserting said volumetric portion into a vertically disposed cuvette for optical analysis, the weight of said volumetric portion being determined and stored for use in calculating the analysis of said solution, determining optical absorption data of said solution by passing a light beam along the longitudinal vertical axis of said cuvette through the total volumetric portion of said solution from one end of said cuvette vertically to its other end having a predetermined cross-section area and then to a detector, said light beam after passing vertically through said total volumetric portion of said solution being then measured for the amount of absorption by said detector, and then determining the analysis of said solution from said absorption data and said weight measurement by feeding said optical data and the weight measurement to a computer, the analysis in the desired units being determined by said computer in accordance with the equation $A = \epsilon \cdot l \cdot c$; where A = absorbance (log Io/I;

$\epsilon$ = molar absorptivity;

l = length of light path passing longitudinally through the solution in the cuvette; and c = the concentration of the absorbing substance;

wherein $c = m/V$ and $l = V/a$ in which m = mass of absorbing substance;

v = the volume of the solution in the cuvette; and a = the cross-section area of the other end of said cuvette.

2. The method of claim 1, wherein the gravimetric measurement is determined by the difference in weight between the cuvette and the cuvette with the volumetric portion therein, the weight thus determined being then stored in said computer along with said optical data to provide analysis of the solution in the desired units.

3. The method of claim 1, wherein the optical measurement determined by passing the light beam longitudinally through the solution in said cuvette utilizes a cuvette with an optical window at its bottom and a free surface at its opposite end, said light beam passing through said optical window and vertically through the total volumetric portion of the solution therein out through the free surface thereof, such that any variation in the volume of said solution added to said cuvette is compensated for by inverse variation in concentration of said substance without varying the light absorption characteristics of said solution.

4. The method of claim 3, wherein the light beam is passed longitudinally and vertically through the solution from the free surface end of the cuvette out through the optical window at its bottom.

* * * * *